US009724457B2

(12) United States Patent
Randall et al.

(10) Patent No.: US 9,724,457 B2
(45) Date of Patent: Aug. 8, 2017

(54) DIALYSIS SERVICE BOX

(71) Applicant: WD MANOR MECHANICAL CONTRACTORS, INC., Phoenix, AZ (US)

(72) Inventors: Jeff Randall, Glendale, AZ (US); Bryan Dewitt, Mesa, AZ (US); Peter Dewitt, Mesa, AZ (US); Rick Garcia, Glendale, AZ (US); Don Gustafson, Tempe, AZ (US)

(73) Assignee: W.D. Manor Mechanical Contractors, Inc., Phoenix, AZ (US)

( * ) Notice: Subject to any disclaimer, the term of this patent is extended or adjusted under 35 U.S.C. 154(b) by 232 days.

(21) Appl. No.: 14/486,523

(22) Filed: Sep. 15, 2014

(65) Prior Publication Data

US 2015/0000758 A1  Jan. 1, 2015

Related U.S. Application Data

(63) Continuation-in-part of application No. 13/180,438, filed on Jul. 11, 2011, now Pat. No. 8,834,718.
(Continued)

(51) Int. Cl.
*A61M 1/16* (2006.01)
*A61M 39/22* (2006.01)
(Continued)

(52) U.S. Cl.
CPC .......... *A61M 1/168* (2013.01); *A61M 1/1656* (2013.01); *A61M 1/1664* (2014.02); *B01D 61/30* (2013.01); *E03B 7/095* (2013.01); *E03C 1/021* (2013.01); *E03C 1/04* (2013.01); *E03C 1/10* (2013.01); *Y10T 137/0402* (2015.04); *Y10T 137/2564* (2015.04)

(58) Field of Classification Search
None
See application file for complete search history.

(56) References Cited

U.S. PATENT DOCUMENTS 1,809,958 A * 6/1931 Wright ................... F25B 17/00
                                                    62/190
3,879,096 A * 4/1975 Blodee .................. A47B 47/05
                                                    312/257.1

(Continued)

FOREIGN PATENT DOCUMENTS

GB              483755 A  *  4/1938  ............. D06F 45/26

*Primary Examiner* — Terry Cecil
(74) *Attorney, Agent, or Firm* — Jennings, Strouss & Salmon, PLC; Michael K. Kelly

(57) ABSTRACT

A dialysis service box for centralized control and plumbing arrangement of a dialysis machine is disclosed. The dialysis service box includes a plumbing arrangement with a warm water inlet and a cold water inlet in fluid flow communication with a temperature mixing component. The thermostatic mixing component mixes the cold water and the warm water to produce mixed water maintained at a predetermined temperature between the temperature of the cold water and the temperature of the warm water. The dialysis service box can be universally installed to operate, control and adjust any dialysis machine that requires supply connection, waste connection, backflow preventer, thermostatic mixing component, a trap primer, or any combination of the foregoing.

14 Claims, 6 Drawing Sheets

Related U.S. Application Data

(60) Provisional application No. 61/363,084, filed on Jul. 9, 2010.

(51) Int. Cl.
*B01D 61/30* (2006.01)
*E03B 7/09* (2006.01)
*E03C 1/02* (2006.01)
*E03C 1/04* (2006.01)
*E03C 1/10* (2006.01)

(56) References Cited

U.S. PATENT DOCUMENTS

| | | | | |
|---|---|---|---|---|
| 5,591,344 | A | * | 1/1997 | Kenley ............ A61L 2/04 210/134 |
| 6,021,805 | A | * | 2/2000 | Horne ............ E03B 7/077 137/375 |
| 7,766,026 | B2 | * | 8/2010 | Boey ............ E03C 1/057 137/1 |
| 2008/0302988 | A1 | * | 12/2008 | Vilendre ............ E03C 1/12 251/129.09 |

\* cited by examiner

DIALYSIS SERVICE BOX

CROSS REFERENCE TO RELATED APPLICATIONS

This application is a continuation-in-part that claims benefit to U.S. non-provisional application Ser. No. 13/180,438 filed on Jul. 11, 2011, now U.S. Pat. No. 8,834,718, which claims benefit to U.S. Provisional Application Ser. No. 61/363,084 filed on Jul. 9, 2010, which are herein incorporated by reference in their entirety.

FIELD

The present disclosure relates to dialysis service box, and in particular to a dialysis service box for providing a centralized compact plumbing connection service box for one or more medical dialysis machines that includes a thermostatic mixing function.

BACKGROUND

The dialysis process and procedure is performed by medical care providers in a hospital or other healthcare facility in which an individual to be treated undergoes a process for removing waste and excess water from the blood, and is primarily used to provide an artificial replacement for lost kidney function in individuals with renal failure. In almost all cases the medical care provider utilizes a dialysis machine in which the plumbing connection to the dialysis machine typically requires potable, untreated city tap water for supply to the dialysis machine and a waste drain for receiving waste from the dialysis machine as the individual undergoes treatment. As shown in FIG. 1, a prior art dialysis service system 10 for performing dialysis requires a single service box with a hose bib and drain connection 14 for supplying a water source and removing waste from the dialysis machine. In addition, the prior art hose bib and drain connection 14, in some jurisdictions, may requires a backflow preventer 18 for preventing retrograde flow of contaminated water and trap primer 16 for insuring periodic priming of the waste outlet to prevent the backflow of waste gases. As shown, the backflow preventer 18 and trap primer 16 are located at remote and separate locations relative to the hose bib and drain connection 14, therefore requiring extensive plumbing be installed to interconnect all of the components of the prior art dialysis service system 10.

With the thermostatic mixing valve at a separate remote location, numerous drawbacks exist in the current configuration of the prior art dialysis service system 10 which requires multiple dialysis services system locations. In particular, water brought to a predetermined temperature at a location remote from the dialysis box may result in a change in water temperature since the water being supplied to the dialysis box must travel a long distance between the remote thermostatic mixing valve to the dialysis box.

In addition, there is the inconvenience and cost in interior design and installation of the plumbing infrastructure that increases the expense to install separate thermostatic mixing component for mixing warm and cold water to maintain the water supplied to various dialysis boxes at a predetermined temperature. There is also an increased cost in maintenance and operation in that the existing designs require more wall space, material, labor, and time to install and operate the necessary additional plumbing 12 that must run between one or more remote thermostatic temperature mixers of the prior art dialysis system 10. Therefore, there is a need in the art for a dialysis service box that addresses these deficiencies in the prior art dialysis service system 10.

SUMMARY

In one embodiment, a dialysis service box may include a casing having a top side portion, a bottom side portion, a rear side portion, a left side portion and a right side portion that collectively define an enclosure. A water supply inlet is attached to the casing and is in communication with a source of fluid, while a waste outlet is also attached to the casing with the waste outlet being in fluid flow communication with a waste disposal. A dialysis supply and waste management system is also disposed within the enclosure of the casing and may include a plumbing arrangement in fluid flow communication with the cold water inlet in fluid flow communication with a source of cold water and a warm water inlet in fluid flow communication with a source of warm water at a first end of the plumbing arrangement in which the cold water inlet and warm water inlet are in fluid flow communication with a thermostatic mixing component, wherein the thermostatic mixing component mixes the cold water and the warm water to produce a mixed water maintained at a predetermined temperature between the temperature of the cold water and the temperature of the warm water, and the plumbing arrangement having a connection port at a second end of the plumbing arrangement configured to provide the mixed water at the predetermined temperature to a dialysis machine.

In yet another embodiment, a method of manufacturing a dialysis service box may include:
  forming a casing having a top side portion, a bottom side portion, a left side portion, an opposing right side portion, and a rear side portion for defining an enclosure;
  installing a plumbing arrangement within the enclosure of the casing in which the plumbing arrangement includes a first end in fluid flow communication with a cold water inlet that communicates with a source of cold water and a warm water inlet that communicates with a source of warm water and a second end of the plumbing arrangement having a connection port configured to be in fluid flow communication with a dialysis machine; and
  installing a thermostatic mixing component within the enclosure of the casing and in communication with the plumbing arrangement such that the thermostatic mixing component is in fluid flow communication with the warm water from the warm water inlet and the cold water from the cold water inlet, wherein the thermostatic mixing component mixes the cold water and the warm water to produce a mixed water maintained at a predetermined temperature between the temperature of the cold water and the temperature of the warm water.

BRIEF DESCRIPTION OF THE DRAWINGS

Corresponding reference characters indicate corresponding elements among the various views of the drawings. The headings used in the figures should not be interpreted to limit the scope of the claims.

DETAILED DESCRIPTION

As described herein, a dialysis service box and method of manufacturing and using the dialysis service box is configured and arranged to provide a centralized control and plumbing arrangement of dialysis machines. The dialysis service box can be universally installed in a convenient location to operate, control, and adjust any connected dialysis machine that requires a potable water supply connection, waste outlet connection, backflow preventer, thermostatic mixing component, and trap primer. In addition, a method of retrofitting the dialysis service box to one or more existing dialysis machines to optimize operation, reduce the cost of maintenance, ease the control and adjustment of the water temperature supply and waste disposal of the dialysis machine is described.

Figure 1:
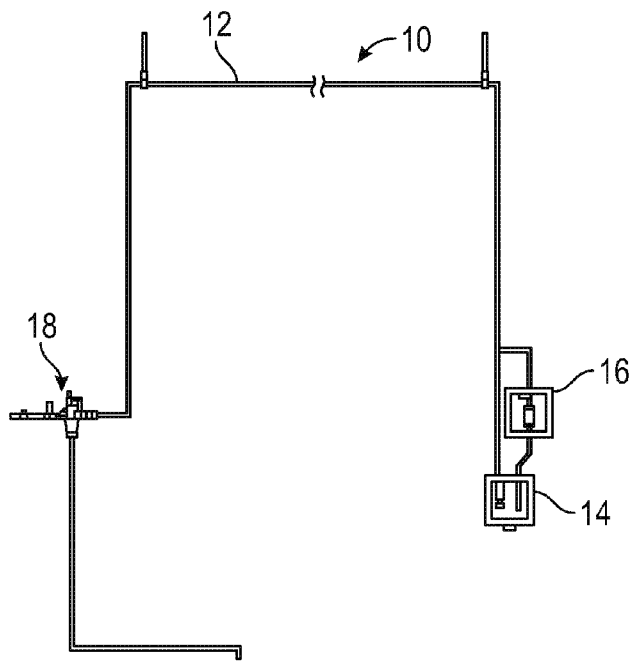
FIG. 1 is a simplified illustration showing a prior art dialysis service system.
Figure 2:
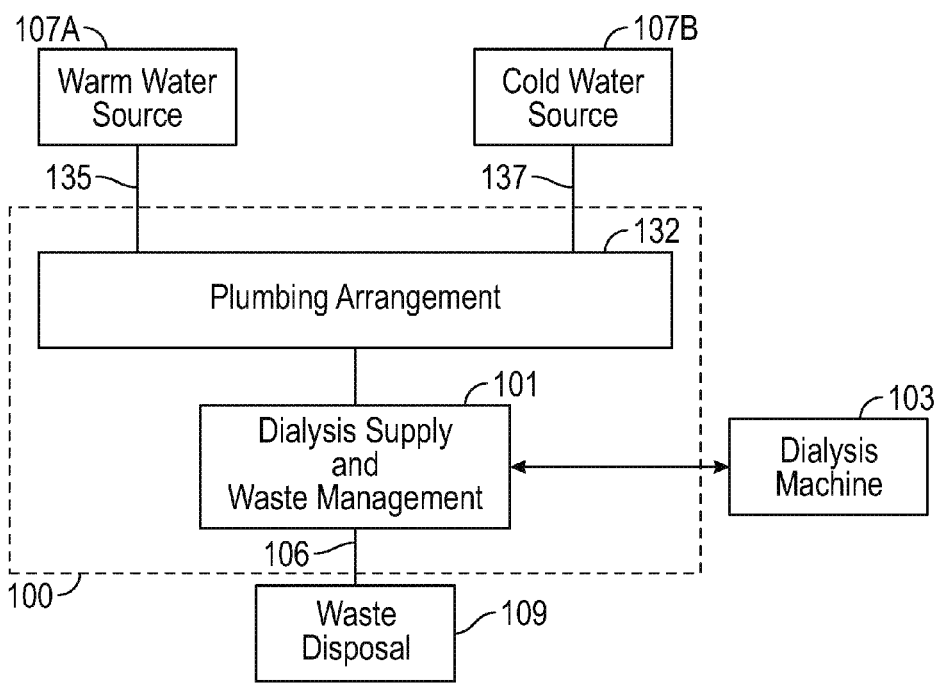
FIG. 2 is a simplified block diagram showing a dialysis service system having a dialysis service box connected to a dialysis machine in a hospital room setting.

Referring to the drawings, an embodiment of the dialysis service box is illustrated and generally indicated as 100 in FIGS. 2-8. In general, as shown in FIG. 2, the dialysis service box 100 manages the flow of potable water from a public water supply including a source of warm water 107A and a source of cold water 107B to the dialysis service box 100 and waste disposal system 109 for disposal of waste products from a dialysis machine 103 which is in fluid flow communication with the dialysis service box 100. In one embodiment, the dialysis service box 100 may be recessed within the wall of a hospital room or other healthcare facility to provide convenient access for connection of the dialysis service box 100 to the dialysis machine 103; however in other embodiments the dialysis service box 100 may be wall or cabinet mounted. In operation, the dialysis service box 100 is configured to be universally installed to operate, control, and adjust any dialysis machine 103 that requires a supply connection, waste connection, thermostatic mixing function, reduced pressure backflow preventer, thermostatic mixing, and trap priming as shall be discussed in greater detail below.

Figure 3:
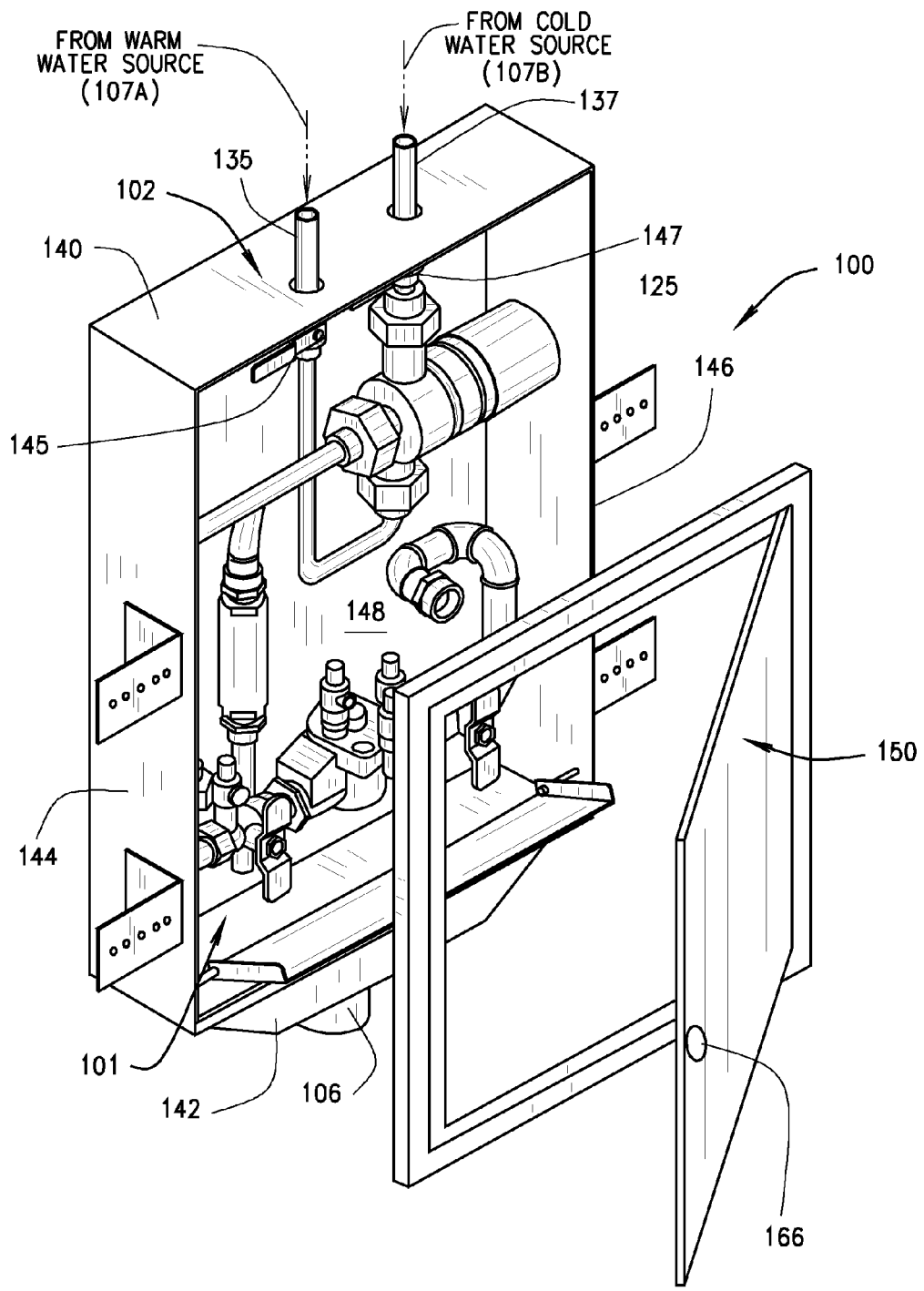
FIG. 3 is a perspective view of one embodiment of a dialysis service box.

Referring to FIG. 3, the dialysis service box 100 includes a casing 102 having a door assembly 150 that communicates with an enclosure defined by the casing 102 for housing a dialysis supply and waste management system 101 having various components that manage the water supply and waste disposal operations for the dialysis machine 103. As shown, the casing 102 includes a warm water inlet 135 and cold water inlet 137 coupled to plumbing arrangement 132 of the dialysis service box 100 that transports a supply of warm and cold water from a respective warm water source 107A and cold water source 107B, for example originating from a public water supply system, to the dialysis service box 100. A waste outlet 106 is in communication with a fixture drain (not shown) for allowing waste received from the dialysis machine 103 to exit the dialysis service box 100 for proper disposal in the waste disposal system 109, such as a public sewer system.

Figure 5:
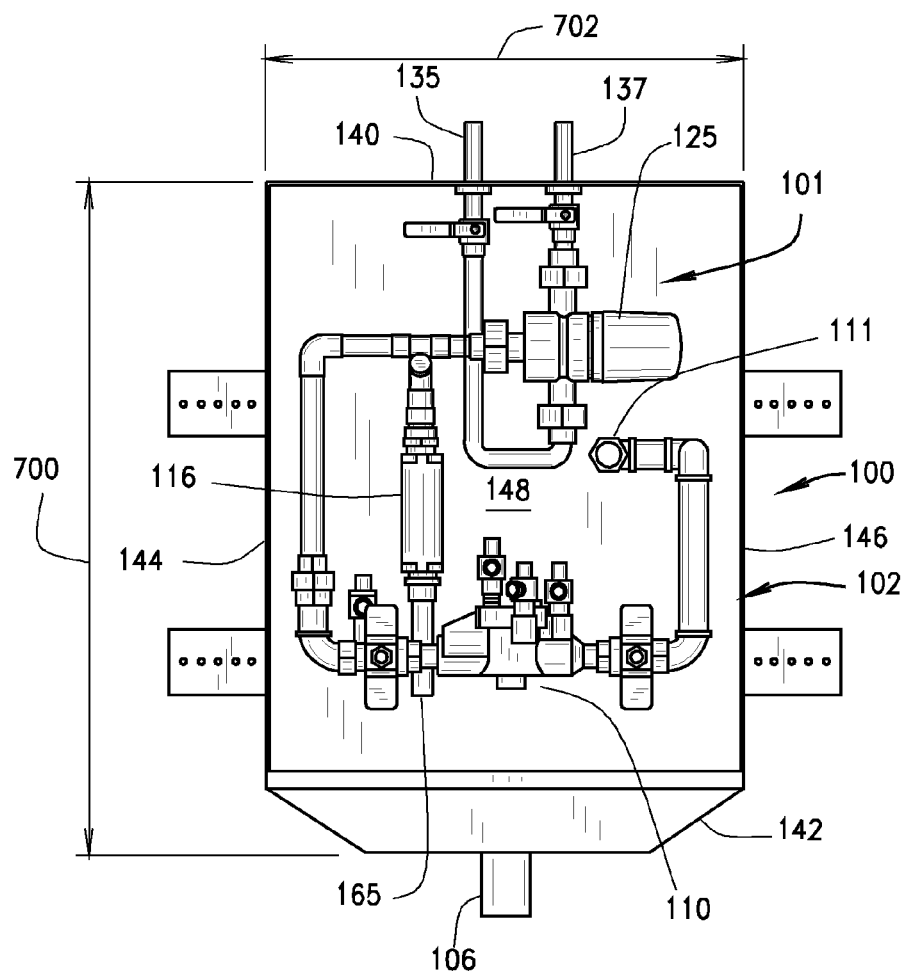
FIG. 5 is a front view of the dialysis service box showing the dimension of the casing that houses the dialysis supply and waste system.
Figure 6:
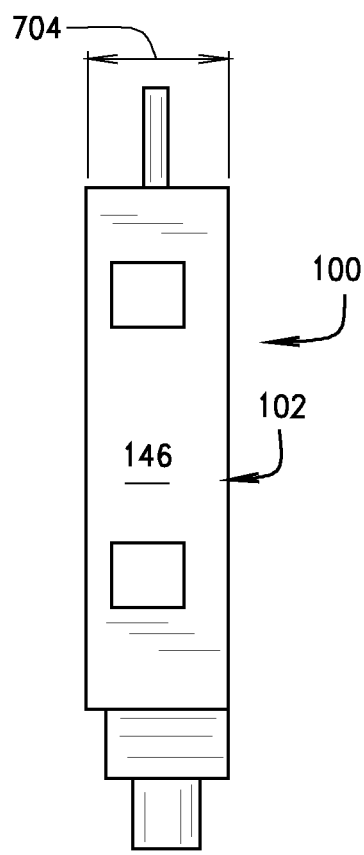
FIG. 6 is a side view of the dialysis service box.
Figure 7:
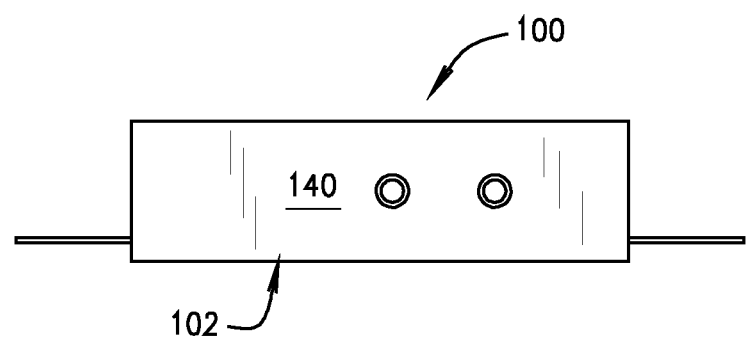
FIG. 7 is a top view of the dialysis service box.

Referring to FIGS. 5-7, the casing 102 forms a top side portion 140, a bottom side portion 142, a left side portion 144, a right side portion 146, a rear portion 148, and a door assembly 150 that collectively define the enclosure for housing the various components of the dialysis supply and waste management system 101 of the dialysis service box 100. The door assembly 150 may include a knob 166 for opening and closing the door assembly 150. In one embodiment, the casing 102 may have a generally rectangular or square-shaped configuration. For example, the casing 102 may have a length 700 of about 17 inches, a width 702 of about 17 inches, and a depth 704 of about 4 inches. In some embodiments, the dialysis service box 100 may have a length 700 between 15 to 20 inches, a width 702 between 15 to 20 inches, and a depth 704 between 2 to 6 inches. In one embodiment, the bottom side portion 142 may have a tapered configuration that channels liquids, such as water and waste, into the waste outlet 106. In some embodiments, the casing 102 may be a recessed box built with a combination of bent and welded 18 gauge stainless steel with the door assembly 150 being made from a separate pre-manufactured stainless steel. The apparatus, articles of manufacture, and methods described herein are not limited in this regard.

Figure 4:
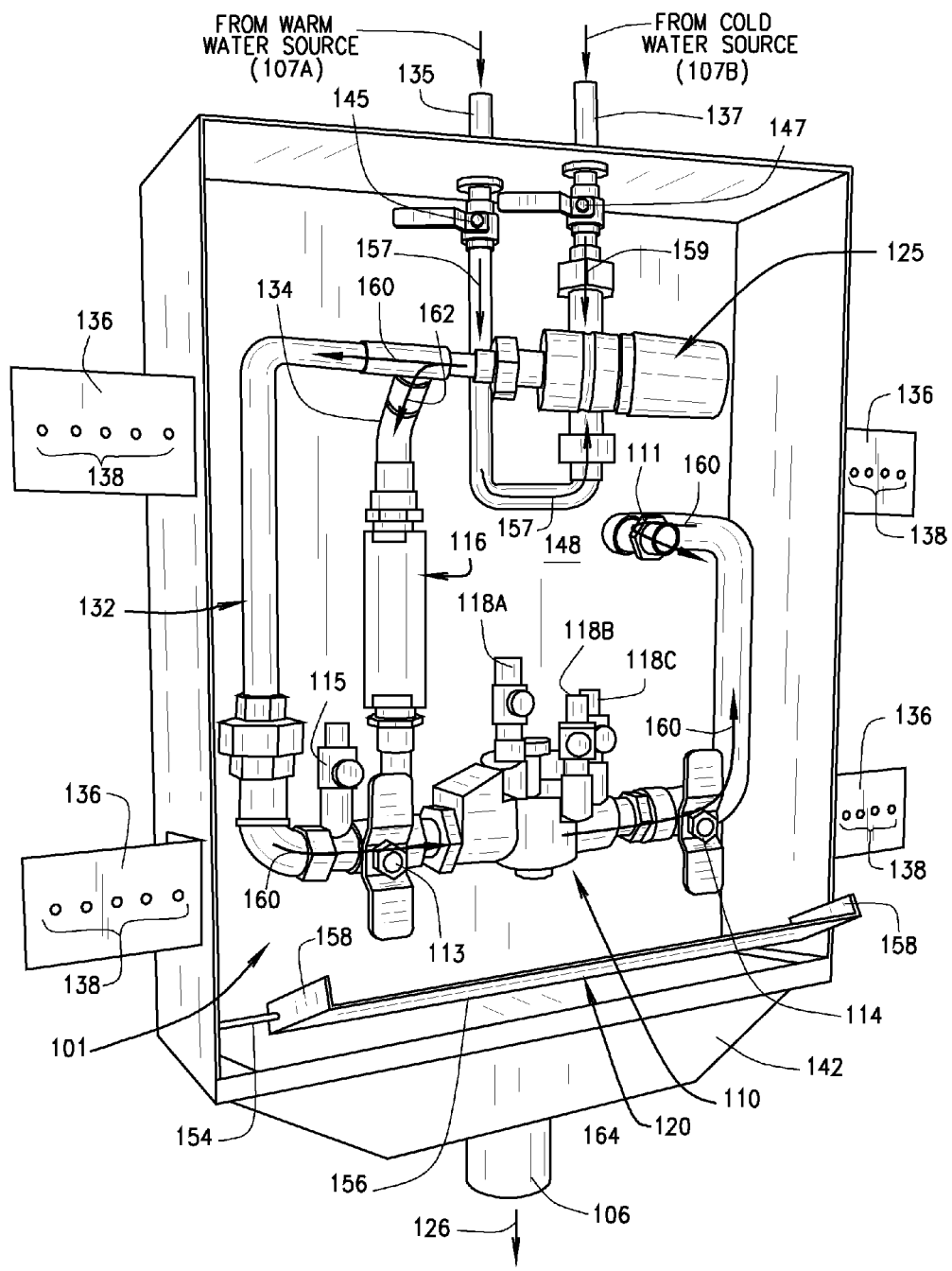
FIG. 4 is a perspective view of the dialysis service box illustrating the various components of a dialysis supply and waste system.

Referring to FIG. 4, the dialysis supply and waste management system 101 includes various components for the management of the water supply and waste disposal operations for the dialysis service box 100. In some embodiments, the dialysis supply and waste management system 101 includes a backflow preventer 110 for preventing retrograde flow of liquid back through the plumbing arrangement 132 of the dialysis supply and waste system 101, a trap primer 116 to insure periodic priming of a p-trap (not shown) that is connected to the waste outlet 106 in fluid flow communication with the waste disposal system 109 to prevent the backflow of waste gases back into the dialysis service box 100, and a thermostatic mixing component 125 for blending the warm water with the cold water to produce mixed water at a predetermined temperature. In addition, first, second, third, and fourth shut-off valves 113, 114, 145 and 147 are provided for preventing fluid flow communication at various points along the plumbing arrangement 132 of the dialysis supply and waste management system 101. In some embodiments, the shut-off valves 113, 114, 145 and 147 may each be a ½" copper ball valve configured to permit or prevent fluid flow communication through plumbing arrangement 132 when actuated.

Referring to FIGS. 3-5, as noted above the dialysis service box 100 includes a warm water inlet 135 that communicates with an external warm water source 107A and an external cold water inlet 137 that communicates with the cold water source 107B for providing separate fluid flows 157 (warm water) and 159 (cold water) through the plumbing arrangement 132 and into the thermostatic mixing component 125. As noted above, the thermostatic mixing component 125 blends the warm water with the cold water such that mixed water is produced at a predetermined temperature that is between the temperature of the cold water and the temperature of the warm water. For example, the temperature of the mixed water that is produced by the thermostatic mixing component 125 may be about 77° F., although the mixed water may be at any predetermined temperature that is between the temperature of the warm water and the temperature of the cold water depending on the geographical location of the public water supply that provides the cold water source 107B to the dialysis service box 100. For instance, the cold water from the cold water source 107B in a geographical location that is colder than normal during the winter will require the thermostatic mixing component 125 to blend warmer water than usual from the warm water source 107A with the colder water from the cold water source 107B to achieve the optimum temperature for the mixed water, while cold water from a cold water source 107B in a geographical location that is extremely warm during the winter will require the thermostatic mixing component 125 to blend less warmer water from the warm water source 107A with the cold water from the cold water source 107B to achieve the optimum temperature for the mixed water.

In some embodiments, the thermostatic mixing component 125 may be any type of thermostatic mixing valve that blends hot or warm water with cold water to ensure constant flow of tempered water at an optimum predetermined temperature. By way of example and not limitation, the thermostatic mixing component 125 may be thermostatic mixing valve, such as ½ inch LFMMV-US-MI model manufactured by Watts Industries.

In one aspect, the thermostatic mixing component 125 allows each individual dialysis service box 100 to separately raise the temperature of the cold water from the cold water source 107B to achieve an optimum temperature by thermostatically mixing in the warm water from the warm water source 107A into the cold water from the cold water source 107B as described above. In this manner, the optimum temperature for the mixed water may be individually set for each respective dialysis service box 100 rather than receiving tempered water from a common source that is distributed to various remote dialysis services boxes.

In one arrangement, the fourth shut-off valve 145 may be positioned along the plumbing arrangement 132 to permit or prevent fluid flow communication between the warm water source 107A and the thermostatic mixing component 125. In addition, a fifth shut-off valve 147 may be positioned along the plumbing arrangement 132 to permit or prevent fluid flow communication between the cold water source 107B and the thermostatic mixing component 125.

As further shown, the reduced pressure backflow preventer 110 prevents retrograde flow of liquid back through the plumbing arrangement 132 of the dialysis service box 100. In one embodiment, the reduced pressure backflow preventer 110 is a testable backflow preventer that falls under the UPC code requirement for most cities and municipalities to protect the potable water supply from possible contaminants generated by the dialysis machine 103 that can be caused if retrograde flow of liquids were allowed to occur. In addition, the reduced pressure backflow preventer 110 includes a dump port 164 that allow for water to exit in case of retrograde flow of liquid due to a loss of water pressure or mechanical failure of the reduced pressure backflow preventer 100. As shown, the reduced pressure backflow preventer 110 includes a plurality of test ports, designated 118A, 118B and 118C, which are configured to engage a testing device designed to test and ensure the proper operation of the reduced pressure backflow preventer 110. In one embodiment, the reduced pressure backflow preventer 110 may be a ½" WATTS 009QT RP Assembly 1, although other suitable types of reduced pressure backflow preventers may be utilized.

The trap primer 116 is in fluid flow communication with plumbing arrangement 132 for insuring periodic priming of the p-trap to prevent waste gases from flowing back into the dialysis service box 100 by allowing sufficient wetting of the p-trap by the gravity flow of water or water droplets into the p-trap through an aperture 165 (FIG. 5) formed at the lower end of the trap primer 116. In one embodiment, the trap primer 116 may be a ½" MIFAB Trap Primer 2 designed to meet UPC code requirements. In addition, the casing 102 may include a drip deflection tray 120 mounted proximate the bottom side portion 142 which is engaged between the right side portion 144 and left side portion 146 of the casing 102 and is configured to deflect any liquid that may drip from between the fittings of the plumbing arrangement 132 or other components of the dialysis supply and waste management system 101. The drip deflection tray 120 forms a tray body 156 defining opposing side walls 158 with a pair of rods 154 attached or integral with the opposing side walls 158 of the tray body 156 that are engaged to the right and left side portions 144 and 146 of the casing 102. The rods 154 of the tray body 156 are configured to swivel such that the drip deflection tray 120 may be positioned between a folded position when the door assembly 150 is closed and in an extended position to when the door assembly 150 is open to prevent spillage of liquid outside the casing 102. In one embodiment, the drip deflection tray 120 may be made from stainless steel.

In addition, a connection port 111 is located at a second end of the plumbing arrangement 132 to exit waste fluids from the dialysis service box 100. The connection port 111 may include a male adapter configured to engage a female adapter (not shown) of the dialysis machine 103. As illustrated, the fluid pathway of water, designated 160, travels from the thermostatic mixing component 125 through the plumbing arrangement 132 of the dialysis service box 100. In addition, a portion of fluid pathway 160, designated fluid pathway 162, may be diverted to the trap primer 116 for supplying the trap primer 116 sufficient water to prime the p trap as discussed above through a second plumbing arrangement 134 coupled to the plumbing arrangement 132. A bleed port 115, for example a pressure relief valve, is in communication with the plumbing arrangement 132 to provide a means for bleeding excess pressurized water if the pressure of the water within the plumbing arrangement 132 exceeds a predetermined threshold. In some embodiments, the pressure of the water flowing through the plumbing arrangement 132 may be 80 psi, or preferably 50 psi, although the pressure of the water may range between 40-80 psi.

Referring back to FIGS. 4 and 5, the casing 102 may include four mounting tabs 136 having a plurality of apertures 138 for receiving a screw, nail or other suitable means of attachment (not shown) such that the casing 102 may be secured within a recess formed inside a wall of a hospital room or mounted directly on the wall or a cabinet.

In one embodiment, the warm water inlet 135 and cold water inlet 137 may both be a ½" copper type "L" tube configured to permit sufficient flow of water into the plumbing arrangement 132. The plumbing arrangement 132 may include a ½" copper tee that permits diversion of second flow pathway 162 the second plumbing arrangement 134 having a ½" copper type "L" tube that is coupled to a ½" copper female adapter engaged to the trap primer 116. In addition, a ½" copper male adapter may be engaged to the opposite end of the trap primer 116 coupled to another ½" copper type "L" tube defining aperture 165 for permitting gravity flow of liquid into the waste disposal 109. As shown, a ½" copper type "L" tube may be coupled between the ½" copper tee and a ½" copper 90, which is engaged to another ½" copper type "L" tube. A ½" copper FIP brass union is interposed between the ½" copper type "L" tube and a ½" brass street 90. In some embodiments, a ½" brass 90 may be coupled to a ½"×2½" brass nipple between the reduced pressure backflow preventer 116 and the connection port 111. Moreover, a ½" brass 90 may be connected between the ½"×2½" brass nipple and a ½" brass street 90, which is coupled to a ½" brass 90 for engagement with the connection port 111.

Figure 8:
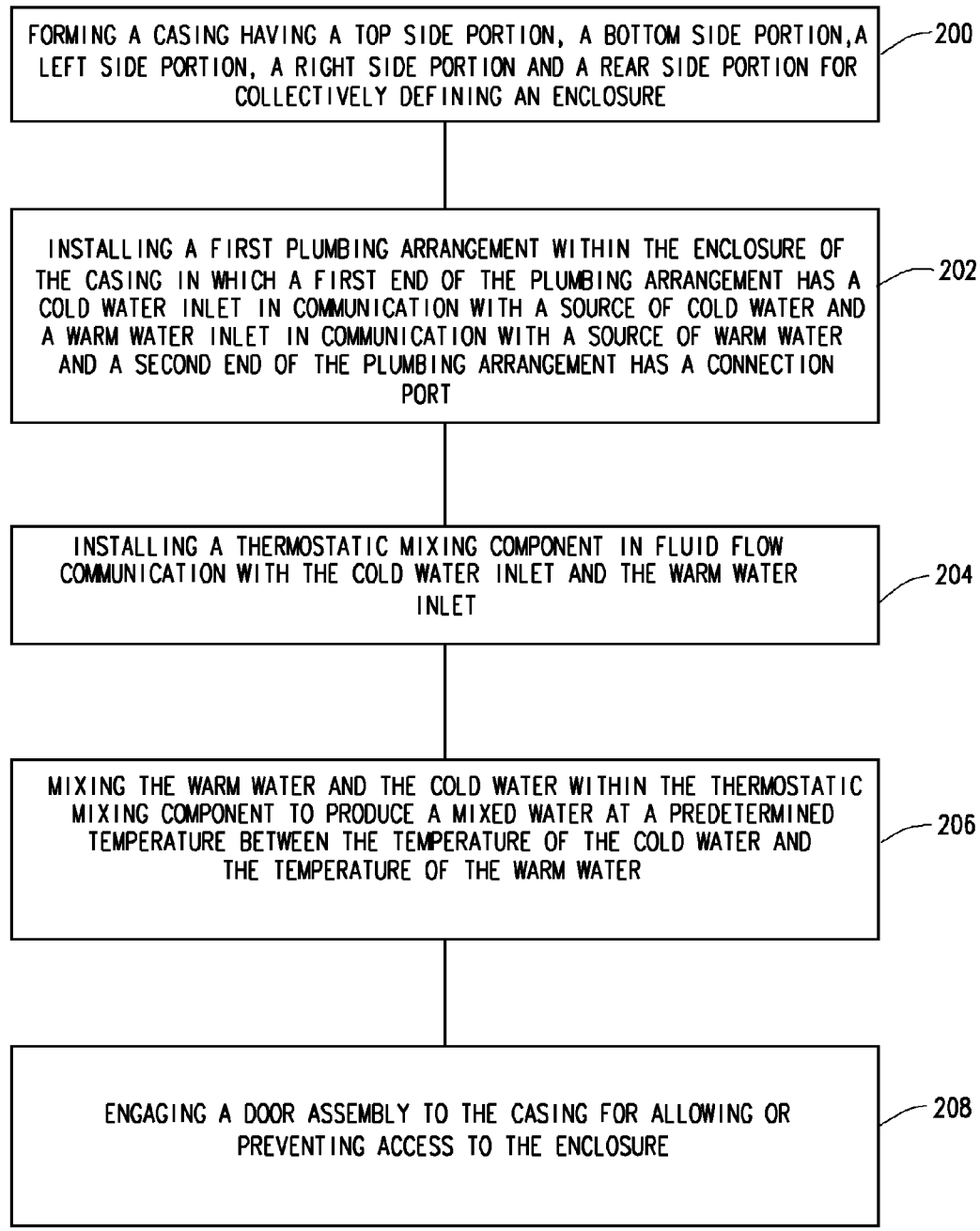
FIG. 8 is a flow chart illustrating one method for manufacturing the dialysis service box.

Referring to FIG. 8, a flow chart illustrates one method for manufacturing the dialysis service box 100. At block 200, forming the casing 102 having a top side portion 140, a bottom side portion 142, a left side portion 144, an opposing right side portion 146, and a rear portion 148 for defining an enclosure. At block 202, installing a first plumbing arrangement within the enclosure of the casing in which a first end of the plumbing arrangement has a cold water inlet in communication with a source of cold water and a warm water inlet in communication with a source of warm water, and a second end of the plumbing arrangement having a connection port. At block 204, installing a thermostatic mixing component 125 in fluid flow communication with the cold water inlet and the warm water inlet. At block 206, mixing the warm water and the cold water within the thermostatic mixing component 125 to produce mixed water at a predetermined temperature between the temperature of the cold water and the temperature of the warm water. At block 208, engaging a door assembly 150 to the casing 102 for allowing or preventing access to the enclosure.

It should be understood from the foregoing that, while particular embodiments have been illustrated and described, various modifications can be made without departing from the spirit and scope of the invention as will be apparent to those skilled in the art. Such changes and modifications are within the scope and teachings of this invention as defined in the claims appended hereto.

What is claimed is:

1. A dialysis service box comprising:
   a casing having a top side portion, a bottom side portion, a rear side portion, a left side portion and a right side portion that collectively define an enclosure;
   a warm water supply inlet attached to the casing;
   a cold water supply inlet attached to the casing;
   a waste outlet attached to the casing, the waste outlet being in fluid flow communication with a waste disposal; and
   a dialysis supply and waste management system disposed within an enclosure defined by the casing, the dialysis supply and waste management system comprising:
      a plumbing arrangement in fluid flow communication with the cold water supply inlet and the a warm water supply inlet;
      a temperature mixing valve in fluid flow communication with the plumbing arrangement, wherein the temperature mixing valve is configured to mix the cold water from the cold water supply inlet and the warm water from the warm water supply inlet to produce a mixed water maintained at a predetermined temperature between the temperature of the cold water and the temperature of the warm water;
      a connection port in fluid flow communication with the temperature mixing valve and configured to provide the mixed water at the predetermined temperature to a dialysis machine;
      a backflow preventer in fluid flow communication with the plumbing arrangement for preventing retrograde flow of a fluid through the plumbing arrangement; and
      a trap primer in fluid flow communication with the plumbing arrangement and including an aperture spaced above the waste outlet for gravity flow communication therewith.

2. The dialysis service box of claim 1, wherein the casing further comprises a drip deflection tray disposed proximate to the bottom side portion of the casing.

3. The dialysis service box of claim 2, wherein the drip deflection tray is mounted to the left side portion and right side portion in a swivel motion such that the drip deflection tray is positioned between a closed position and an extended position.

4. The dialysis service box of claim 1, wherein the backflow preventer is in fluid flow communication with the temperature mixing valve, wherein the backflow preventer comprises a reduced pressure backflow preventer having at least one test port for testing the operation of the backflow preventer.

5. The dialysis service box of claim 4, wherein the backflow preventer further comprises a dump port for allowing a retrograde flow of the fluid to exit the plumbing arrangement.

6. The dialysis service box of claim 1, wherein the casing includes a door assembly for permitting or preventing access to the enclosure.

7. The dialysis service box of claim 1, wherein the trap primer is configured to supply the mixed water to the waste outlet to prevent a waste gas from flowing into the plumbing arrangement.

8. The dialysis service box of claim 1, wherein the plumbing arrangement includes a first shut-off valve for preventing fluid flow communication between the temperature mixing valve and the cold water supply inlet, and a second shut-off valve for preventing fluid flow communication between the temperature mixing component and the warm water supply inlet.

9. The dialysis service box of claim 8, wherein the first and second shut-off valves comprise ball valves in operative engagement with a respective handle for preventing or permitting fluid flow communication to the thermostatic mixing component.

10. The dialysis service box of claim 1, wherein the casing further comprises a plurality of mounting tabs for mounting the casing to a surface.

11. A method of manufacturing a dialysis service box comprising:
    forming a casing having a top side portion, a bottom side portion, a left side portion, an opposing right side portion, and a rear side portion for defining an enclosure;
    installing a plumbing arrangement within the enclosure of the casing, the plumbing arrangement including a supply inlet and a connection port configured to be in fluid flow communication with a dialysis machine;
    attaching the plumbing arrangement to a cold water inlet that communicates with a source of cold water and to a warm water inlet that communicates with a source of warm water, and equipping the plumbing arrangement with a connection port configured to be in fluid flow communication with a dialysis machine;
    installing a thermostatic mixing valve within the enclosure of the casing and in communication with the plumbing arrangement such that the thermostatic mixing valve is in fluid flow communication with the warm water from the warm water inlet and the cold water from the cold water inlet, wherein the thermostatic mixing valve mixes the cold water and the warm water to produce a mixed water maintained at a predetermined temperature between the temperature of the cold water and the temperature of the warm water;

installing a trap primer within the enclosure of the casing and in communication with the plumbing arrangement and including an aperture spaced above the waste outlet for gravity flow communication therewith; and installing a backflow preventer within the enclosure of the casing and in fluid flow communication with the plumbing arrangement.

12. The method of claim 11, wherein forming the casing further comprises attaching a door assembly adjacent a portion of the top side portion, bottom side portion, left side portion and opposing right side portion.

13. The method of claim 11, wherein installing a temperature mixing valve within the enclosure comprises positioning the temperature mixing valve in fluid flow communication with the trap primer such that a portion of the mixed water flows into the trap primer.

14. The method of claim 11, wherein installing the plumbing arrangement further comprises installing at least one shut off valve for selectively permitting and preventing fluid flow communication through the plumbing arrangement.

* * * * *